(12) United States Patent
Houze

(10) Patent No.: US 7,867,986 B2
(45) Date of Patent: Jan. 11, 2011

(54) ENHANCED DRUG DELIVERY IN TRANSDERMAL SYSTEMS

(75) Inventor: David Houze, Coconut Grove, FL (US)

(73) Assignee: Noven Pharmaceuticals, Inc., Miami, FL (US)

( * ) Notice: Subject to any disclaimer, the term of this patent is extended or adjusted under 35 U.S.C. 154(b) by 1997 days.

(21) Appl. No.: 10/330,361

(22) Filed: Dec. 30, 2002

(65) Prior Publication Data

US 2003/0152615 A1    Aug. 14, 2003

Related U.S. Application Data

(63) Continuation of application No. 09/948,107, filed on Sep. 7, 2001, now abandoned.

(60) Provisional application No. 60/298,381, filed on Jun. 18, 2001.

(51) Int. Cl.
*A61K 31/56* (2006.01)
(52) U.S. Cl. .................................................. 514/171
(58) Field of Classification Search .................. 514/170, 514/171, 180
See application file for complete search history.

(56) References Cited

U.S. PATENT DOCUMENTS

| | | | |
|---|---|---|---|
| 4,529,601 A | 7/1985 | Broberg et al. | |
| 4,585,452 A * | 4/1986 | Sablotsky | 424/449 |
| 4,906,169 A | 3/1990 | Chien et al. | |
| 5,422,119 A | 6/1995 | Casper | |
| 5,474,783 A | 12/1995 | Miranda et al. | |
| 5,633,242 A | 5/1997 | Oettel et al. | |
| 5,656,386 A | 8/1997 | Scherer et al. | |
| 5,711,962 A | 1/1998 | Cordes et al. | |
| 5,770,219 A * | 6/1998 | Chiang et al. | 424/448 |
| 5,780,050 A | 7/1998 | Jain et al. | |
| 5,811,117 A | 9/1998 | Hashimoto et al. | |
| 5,849,729 A * | 12/1998 | Zoumas et al. | 514/169 |
| 5,898,032 A | 4/1999 | Hodgen | |
| 5,958,446 A * | 9/1999 | Miranda et al. | 424/448 |
| 6,024,974 A | 2/2000 | Li | |
| 6,143,319 A | 11/2000 | Meconi et al. | |

(Continued)

FOREIGN PATENT DOCUMENTS

CL    49-95    1/1994

(Continued)

OTHER PUBLICATIONS

M.D. Mashkovsky, The Medicaments, Guidelines for Medical Doctors, vol. 1, 2001, 2 pgs., translation provided.

(Continued)

*Primary Examiner*—San-ming Hui
(74) *Attorney, Agent, or Firm*—Foley & Lardner LLP

(57) ABSTRACT

A composition for transdermal administration resulting from an admixture includes: a therapeutically effective amount of a pharmaceutically active agent that includes a corresponding steroid and a steroid derivative; and a carrier for the pharmaceutically active agent. The steroid and the corresponding steroid derivative are present in a weight ratio of 10:1 to 1:10 steroid: corresponding steroid derivative. In a preferred embodiment ratio is 6:1 to 1:6. In a preferred embodiment, the corresponding steroid derivative is a steroid ester. In another preferred embodiment, the carrier is a polymer that includes a pressure-sensitive adhesive.

33 Claims, 3 Drawing Sheets

U.S. PATENT DOCUMENTS

| | | | |
|---|---|---|---|
| 6,149,935 | A | 11/2000 | Chiang et al. |
| 6,153,216 | A | 11/2000 | Cordes et al. |
| 6,221,383 | B1 | 4/2001 | Miranda et al. |
| 6,303,141 | B1 | 10/2001 | Fischer et al. |
| 7,456,159 | B2 | 11/2008 | Houze et al. |
| 2003/0152613 | A1 | 8/2003 | Houze |
| 2003/0152614 | A1 | 8/2003 | Houze |
| 2008/0167280 | A1 | 7/2008 | Houze et al. |
| 2008/0167365 | A1 | 7/2008 | Houze et al. |

FOREIGN PATENT DOCUMENTS

| | | |
|---|---|---|
| CL | 50-96 | 1/1995 |
| EP | 0 279 977 | 8/1988 |
| EP | 0 294 601 B1 | 1/1993 |
| WO | WO 90/06736 A1 | 6/1990 |
| WO | WO 94/16709 A1 | 8/1994 |
| WO | WO 98/51283 A1 | 11/1998 |
| WO | WO 99/15156 | 4/1999 |
| WO | WO 99/15156 A1 | 4/1999 |
| WO | WO 99/66907 A1 | 12/1999 |
| WO | WO 01/02015 A1 | 1/2001 |

OTHER PUBLICATIONS

Examiners Report issued Nov. 2008 in Chilean Patent Application No. 1332-2002.

Office Action issued on Apr. 5, 2010 by the Examiner in U.S. Appl. No. 11/979,263 (US 2008/0167280).

Office Action issued on Jul. 17, 2009 by the Examiner in U.S. Appl. No. 11/979,263 (US 2008/0167280).

Office Action issued on Feb. 25, 2009 by the Examiner in U.S. Appl. No. 11/979,263 (US 2008/0167280).

Board of Patent Appeals and Interferences Decision issued on Mar. 16, 2010 by the Examiner in U.S. Appl. No. 10/330,360 (US 2003/0152614).

Board of Patent Appeals and Interferences Decision issued on Mar. 16, 2010 by the Examiner in U.S. Appl. No. 10/330,279 (US 2003/0152613).

Notice of Allowance issued on May 1, 2008 by the Examiner in U.S. Appl. No. 10/330,281 (US 7,456,159).

Office Action issued on Sep. 10, 2007 by the Examiner in U.S. Appl. No. 10/330,281 (US 7,456,159).

Office Action issued on Feb. 8, 2007 by the Examiner in U.S. Appl. No. 10/330,281 (US 7,456,159).

Office Action issued on Jun. 14, 2006 by the Examiner in U.S. Appl. No. 10/330,281 (US 7,456,159).

Office Action issued on Dec. 30, 2005 by the Examiner in U.S. Appl. No. 10/330,281 (US 7,456,159).

Office Action issued on Jun. 29, 2005 by the Examiner in U.S. Appl. No. 10/330,281 (US 7,456,159).

* cited by examiner

ENHANCED DRUG DELIVERY IN TRANSDERMAL SYSTEMS

This application is a continuation of application Ser. No. 09/948,107, filed Sep. 7, 2001, which claims priority to U.S. Provisional Application No. 60/298,381, filed Jun. 18, 2001.

BACKGROUND OF THE INVENTION

1. Field of the Invention

The present invention relates to transdermal drug delivery systems. In particular, the present invention relates to transdermal drug delivery systems for delivering steroids, and to methods of making and using the same.

2. Description of the Related Art

The use of a transdermal drug delivery system, for example a pressure-sensitive adhesive containing a medicament, namely, a drug, as a means for administering therapeutically effective amounts of the medicament is well known. Such known delivery systems involve incorporation of a medicament into a carrier such as a polymeric and/or a pressure-sensitive adhesive formulation or other forms of carriers. The pressure-sensitive adhesive must adhere effectively to the skin and permit migration of the medicament from the carrier through the skin and into the bloodstream of the patient.

Steroids such as estradiol and norethindrone are especially well known for use in transdermal drug delivery systems, in particular, as hormone replacement therapy. These steroids may be administered singularly, such as the estradiol transdermal drug delivery system sold under the trademark Vivelle® and Vivelle-Dot™manufactured by Noven Pharmaceuticals, Inc. of Miami, Fla. See also U.S. Pat. No. 6,221,383. Alternatively, two or more steroids may be administered together, such as the estradiol/norethindrone acetate transdermal drug delivery system sold under the trademark Combi-Patch® also manufactured by Noven Pharmaceuticals. See also U.S. Pat. No. 6,221,383. See also U.S. Pat. No. 5,474,783.

Transdermal drug delivery systems with more than one drug are generally more difficult to formulate in view of different interactions with each drug and the carrier, excipients, etc., even the other drug present. In addition, government agencies that regulate pharmaceutical products, such as the FDA in the United States, require more testing of multiple drugs, individually as well as together to establish efficacy. Thus, when a steroid is administered, it is generally administered in one form only (e.g., norethindrone or norethindrone acetate). See, e.g., U.S. Pat. No. 6,149,935.

The use of a steroid as an additive to act as a crystallization inhibitor in transdermal drug delivery devices where the drug is a hormone is described in WO 99/15156. WO 99/15156 teaches the steroid is present in the device in an amount insufficient to provide significant pharmaceutical or physiological effect. Other patents include U.S. Pat. Nos. 5,633,242; 4,906,169; 5,711,962; 6,153,216; 5,898,032; 5,811,117; and 6,024,974.

One problem in the delivery of steroids from transdermal drug delivery systems lies in the rate of drug release (commonly called "flux" or "permeation rate") from the transdermal system. Specifically, there are many applications in which it would be desirable to have a greater flux of steroid from the system. Another problem in the delivery of steroids is the tendency for steroids to crystallize in the carrier of the transdermal system. This results in less steroid being available for transdermal administration. Although the addition of solublilzing agents, such as PVP, help to inhibit crystallization, there are some applications where it is desirable to have a greater crystal inhibiting effect.

SUMMARY OF THE INVENTION

One object of the invention is to overcome the disadvantages of the known art described above. Another object of the invention is to provide a transdermal drug delivery system that has an improved flux of steroid compared to a system of equal size. Still another object of the invention is to provide a composition that has reduced, or no, crystal formation in the transdermal drug delivery system.

In accomplishing the foregoing and other objects, there has been provided according to one aspect of the present invention a composition, preferably a dermal composition, resulting from an admixture that includes: a therapeutically effective amount of a pharmaceutically active agent that includes a steroid and a corresponding steroid derivative that provides a source of therapeutically active steroid; and a carrier for the pharmaceutically active agent, wherein the steroid and steroid derivative are present in a weight ratio of 10:1 to 1:10 steroid: steroid derivative. In a preferred embodiment, the steroid derivative is a steroid ester. In another preferred embodiment the carrier is a polymer that includes a pressure-sensitive adhesive.

According to another aspect of the invention, there has been provided a method of making a composition described above that includes forming a mixture of the steroid, corresponding steroid derivative and carrier. Preferably, the carrier is a polymer and the method further includes: forming the blend into a polymer matrix; and drying the polymer matrix to remove volatile solvents to form the composition.

According to another aspect of the invention, there has been provided a method of treating a human or an animal with a therapeutically effective amount of a pharmaceutically active agent, that includes the steps of: applying to the skin of an animal or human being, the composition described above; and maintaining the composition in contact with the skin for a predetermined length of time sufficient to administer the therapeutically amount of the active agent.

Further objects, features and advantages of the present invention will become apparent from the detailed description of preferred embodiments which follows.

DETAILED DESCRIPTION OF PREFERRED EMBODIMENTS

Figure 1:
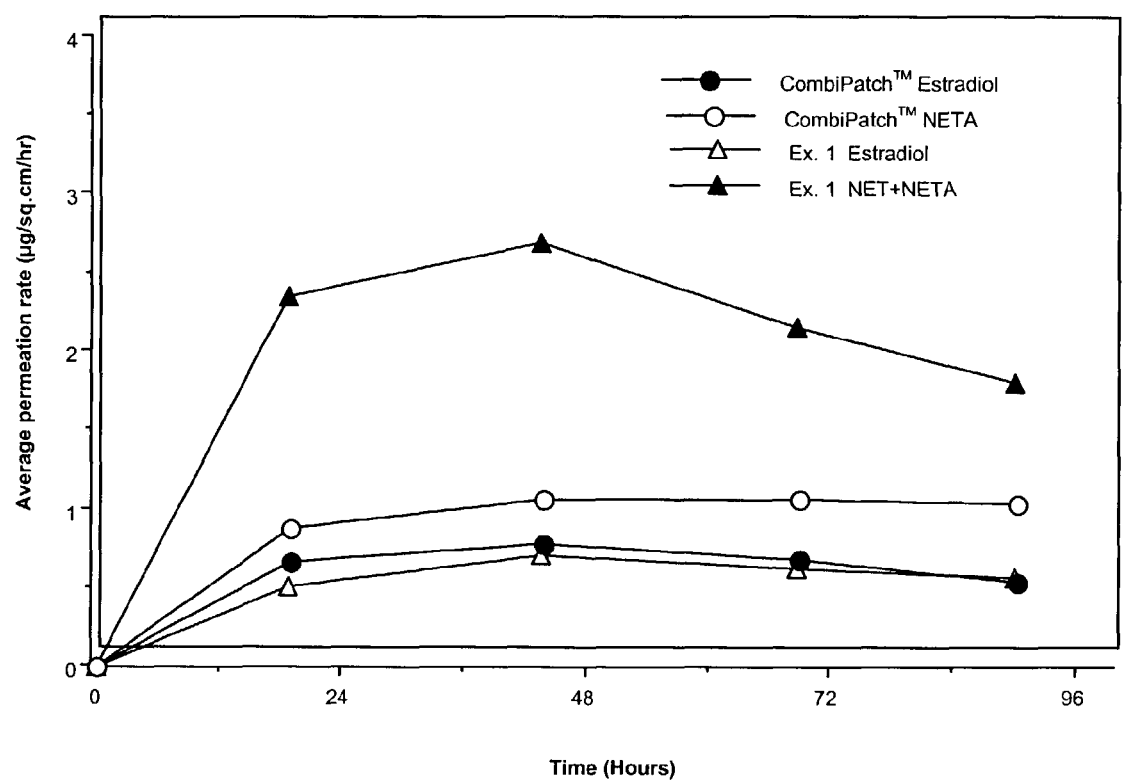
FIG. 1 is a graph illustrating the drug flux from a composition containing norethindrone acetate and estradiol, and a composition containing combined norethindrone/norethindrone acetate and estradiol.

The present invention provides, inter alia, a transdermal drug delivery composition for administration of a therapeutically effective amount of a steroid, particularly transdermal compositions having a greater flux than known compositions.

As used herein, "transdermal" delivery is intended both transdermal (or "percutaneous" or "dermal") and transmucosal administration, i.e., delivery by passage of a drug through the skin or mucosal tissue and into the bloodstream.

As used herein, the term, "flux" (also called "permeation rate") is defined as the absorption of the drug through the skin or mucosa, and is described by Fick's first law of diffusion:

$$J = -D(dCm/dx),$$

where $J$ is the flux in $g/cm^2/sec$, $D$ is the diffusion coefficient of the drug through the skin or mucosa in $cm^2/sec$ and $dCm/dx$ is the concentration gradient of the drug across the skin or mucosa.

As used herein, a steroid is defined as a family of lipid compounds that includes the sterols, bile acids, cardiac glycosides, saponins, corticoid steroids and hormones. The basic structure of the steroid is a well known 4 ring fused structure.

Useful for this invention are steroids having a free hydroxy group at a position on the steroid ring, such as the 17-position, the 3-position, or at the 11-postion on the fused ring. Particularly preferred are hormones such as estrogens, progestins, and androgens. The corresponding steroid derivative is defined as a corresponding structure to the steroid where the free hydroxy at the 3, 11 or 17 postion has been reacted with an alcohol reactive moiety. Particularly preferred are steroid derivatives reacted at the 17 position. Regardless of whether the steroid or the corresponding steroid derivative is incorporated in the carrier composition as the dominant drug, each provides a source of steroid in the bloodstream to achieve the intended physiological effect which, in the case of the corresponding steroid derivative, occurs through metabolic conversion of the derivative.

A steroid ester is the corresponding structure to the steroid where the free hydroxy group on the ring has been esterified. Examples of a steroid and its corresponding ester include estradiol and estradiol benzoate, estradiol 17-beta cypionate, estradiol 17 propionate, estradiol hemisuccinate (eutocol), estradiol enanthate, estradiol undecylate, etc. Another example is testosterone and its corresponding ester of testosterone such as 17 beta-cypionate, testosterone enanthate, testosterone nicotinate, testosterone phenylacetate, testosterone propionate, etc. Also included are non-esters that have groups on the 17 position such as testosterone 17-chloral hemiacetal, or ethers that have groups on the 3-position such as estradiol 3-methyl ether.

Other steroids that can be used include progestins such as allylestrenol, anagestone, desogestrel, dimethisterone, dydrogesterone, ethisterone, ethynodiol, gestodene, haloprogesterone, 17-hydroxy-16-methylene-progesterone, 17.alpha.-hydroxyprogesterone, lynestrenol, medroxyprogesterone, melengestrol, norethindrone, norethynodrel, norgesterone, norgestimate, norgestrel, norgestrienone, norvinisterone, pentagestrone, and trimigestone.

Anabolic steroids can include androisoxazole, androstenediol, bolandiol, bolasterone, clostebol, ethylestrenol. formyldienolone, 4-hydroxy-19-nortestosterone, methandriol, methenolone, methyltrienolone, nandrolone, norbolethone, oxymesterone, stenbolone and trenbolone. Androgenic steroids can include boldenone, fluoxymesterone, mestanolone, mesterolone, methandrostenolone, 17-methyltestosterone, 17.alpha.-methyltestosterone 3-cyclopentyl enol ether, norethandrolone, normethandrone, oxandrolone, oxymesterone, oxymetholone, prasterone, stanlolone, stanozolol, testosterone, testosterone 17-chloral hemiacetal and tiomesterone.

Estrogens can include conjugated estrogenic hormones, equilenin, equilin, estradiol, estradiol benzoate, estradiol 17.beta.-cypionate, estriol, estrone, ethinyl estradiol and mixtures thereof.

Further steroids can include glucocorticoids such as 21-Acetoxyprefnenolone, Aalclometasone, Algestone, Amicinonide, Beclomethasone, Betamethasone, Budesonide, Chloroprednisone, Clobetasol, Blovetasone, Clocortolone, Cloprednol, Corticosterone, Cortisone, Cortivazol, Deflazacort, Desonide, Desoximetasone, Dexamethasone, Diflorasone, Diflucortolone, Difluprednate, Enoxolone, Fluazacort, Flucloronide, Flumehtasone, Flunisolide, Fluocinolone Acetonide, Fluocinonide, Fluocortin Butyl, Fluocortolone, Fluorometholone, Fluperolone, Fluprednidene, Fluprednisolone, Flurandrenolide, Formocortal, Halcinonide, Halometasone, Halopredone, Hydrocortamate, Hydrocortisone, Maziprednone, Medrysone, Meprednisone, Methyolprednisolone, Mometasone Furoate, Paramethasone, Prednicarbate, Prednisolone, Prednisone, Prednival, Prednylidene, Tixocortal, and Triamcinolone, Also included are mineralcorticoids such as Aldosterone, Deoxycorticosterone and Fludrocortisone.

In typical known devices the corresponding steroid derivative is administered in view of crystallizations problems that occur with the use of the non-derivative steroid. The present inventors have discovered that when the steroid is administered together with its corresponding steroid derivative, a synergism in flux is observed as well as a reduction in crystallization. That is, the flux from the combination of steroid and steroid derivative is greater than the flux of an equal amount of steroid or steroid derivative alone. For example, in a system that contains estradiol and norethindrone acetate, the addition of norethindrone and a reduction in the amount of norethindrone acetate such that the combined amount equals the original amount of norethindrone acetate results in increased delivery of norethindrone/norethindrone acetate.

Another unexpected advantage of the present invention is that the total amount of steroid/corresponding steroid derivative delivered from the system is significantly greater than the amount drug from a composition containing the steroid or corresponding steroid derivative alone. For example, applicants have found that for compositions containing both norethindrone acetate and norethindrone, the total amount of steroid delivered from the system was 65% greater than a system containing a comparable amount of norethindrone acetate alone.

In order to achieve this synergistic effect, the weight ratio of steroid/corresponding steroid derivative is important. The ratio is preferably in the range of 10:1 to 1:10 steroid:corresponding steroid derivative. A more preferred ratio is in the range of 6:1 to 1:6 steroid:corresponding steroid derivative. The ratios providing the greatest synergism depend on the pharmaceutically active agents in the system. For example, for the administration of the corresponding steroid and steroid derivative alone, a greater amount of steroid relative to corresponding steroid derivative produces the greatest synergy. In this embodiment, a preferred ratio is 1:1 to 3:1, more preferably 3:2 to 5:2, even more preferably about 2:1. However, when an additional steroid is present (such as estradiol) the opposite ratio gives the greatest synergy. In this embodiment, a preferred ratio is 1:1 to 1:3, more preferably 2:3 to 2:5, even more preferably 1:2 steroid:corresponding steroid derivative. Any ratio that provides a synergistic flux is within the scope of the present invention.

The inventors have also discovered that the combination of a steroid and its corresponding steroid derivative can assist in inhibiting crystallization of the steroid/corresponding steroid derivative in the transdermal composition. This is particularly important for the next generation of transdermal drug delivery systems (particularly for hormone replacement therapy) that will be required to deliver a therapeutically effective amount of the steroid over the course of up to one week or more. To achieve an extended delivery, the steroid must often be incorporated into the composition in a supersaturated state. However, supersaturation often leads to problems of crystallization. The inventors believe that that inclusion of both the steroid and steroid corresponding derivative into the carrier matrix (particularly the polymer matrix) functions to disrupt each entities (i.e., steroid or its corresponding derivative) crystal lattice structure, thus inhibiting crystal formation. Some corresponding derivatives will work better than others in providing this disruption. For example, it has been found that testosterone propionate does not work as well as other testosterone esters. Likewise, estradiol enanthate and propionate work much better than estradiol acetate in combination with estradiol.

Moreover, it further has been found that combinations of steroid derivatives also result in inhibiting crystallization of the drug species in the transdermal carrier compositions, with certain derivatives again working better than others. As shown in Table I, the addition of estradiol methyl ether to estradiol acetate in a transdermal carrier composition significantly improves crystal inhibition, whereas the combination of estradiol acetate and estradiol propionate shows no improvement, at the concentrations tested. The examples were observed through a microscope for crystal formation after two weeks maintained at 25° C. and a relative humidity of 65% to 70%, using a viewing field of 38.5 mm$^2$.

effect, etc. The minimum amount of steroid/corresponding steroid derivative in the system is selected based on the amount of steroid/corresponding steroid derivative which passes through the skin in the time span for which the composition is to provide therapy. Normally, the amount of steroid/corresponding steroid derivative in the composition can vary from about 0.1% to about 50% by weight, and preferably, for the lower steroid/corresponding steroid derivative doses permitted by this invention, from about 0.3% to about 20%. Other possible ranges can include 0.1% to 10%, or 0.1% to 6% by weight.

The steroid is present in a carrier. "Carrier" or "vehicle" as used herein refers to carrier materials suitable for transdermal drug administration, and include any such materials known in the art, e.g., any liquid, gel, solvent, liquid diluent, solubilizer, polymer or the like, which is nontoxic and which does not significantly interact with other components of the composition or the skin in a deleterious manner. The carrier is present in an amount sufficient to achieve its function of carrying the steroid/corresponding steroid derivative. Preferably, the carrier is present in an amount ranging from 2 to 99 wt %, more preferably 30 to 90 wt %, even more preferably 40 to 80 wt %. The carrier is preferably substantially free of water and more preferably contains no water.

Particularly preferred carriers are flexible, finite compositions. The phrase "flexible, finite system" is intended to mean a solid form capable of conforming to the surface with which it comes into contact, and which is capable of maintaining the contact in such solid form so as to facilitate topical application without adverse physiological response, and without being appreciably decomposed by aqueous contact during administration to a patient. Particularly preferred flexible, finite systems are polymer carriers such as pressure-sensitive adhesive matrix type in which the steroid/corresponding steroid derivative is dispersed directly in the pressure-sensitive adhesive or reservoir type carriers.

Illustrative examples of suitable adhesives as matrix type flexible, finite delivery systems include those described in U.S. Pat. Nos. 5,474,783, and 5,656,386 both assigned to

TABLE I

| % INGREDIENT | EXAMPLE A | EXAMPLE B | EXAMPLE C | EXAMPLE D | EXAMPLE E |
|---|---|---|---|---|---|
| Estradiol acetate | 3 | — | — | 3 | 3 |
| Estradiol propionate | — | 3 | — | 3 | — |
| Estradiol methyl ether | — | — | 3 | — | 3 |
| Acrylic Adhesive (GMS 788) | 5 | 5 | 5 | 5 | 5 |
| Oleyl Alcohol | 6 | 6 | 6 | 6 | 6 |
| Dipropylene Glycol | 9 | 9 | 9 | 9 | 9 |
| Silicone Adhesive (BIO-PSA 7-4603) | 75 | 75 | 75 | 72 | 72 |
| Polyvinylpyrrolidone (KOLLIDON-30) | 2 | 2 | 2 | 2 | 2 |
| CRYSTAL FORMATION | ≧100 | Long branched crystals throughout | None | Branched crystals throughout | ≦2 |

Determining which steroid derivatives work better than others in combination with steroids or other steroid derivatives can be determined through routine experimentation using the present specification as a guide.

The combined amount of steroid present in the composition can vary broadly and depends on many factors such as the carrier, the length of administration, desired therapeutic Noven Pharmaceuticals, Inc., Miami, Fla. (incorporated herein by reference in their entireties). Other flexible, finite systems known in the art include films, plasters, dressings, and bandages, as well as multilayer delivery systems in which the steroid/corresponding steroid derivative is solubilized or contained in one or more separate layers and reservoir-type delivery systems in which the steroid/corresponding steroid derivative is solubilized or contained in a reservoir or depot separate form the adhesive which attaches directly to the skin or mucosa.

As noted above, particularly preferred carriers are pressure-sensitive adhesive flexible, finite carriers. These can include any viscoelastic material which adheres instantaneously to most substrates with the application of very slight pressure and remains permanently tacky. A polymer is a pressure-sensitive adhesive within the meaning of the term as used herein if it has the properties of a pressure-sensitive adhesive per se or functions as a pressure-sensitive adhesive by admixture with tackifiers, plasticizers or other additives. The term pressure-sensitive adhesive also includes mixtures of different polymers and mixtures of polymers, such as polyisobutylenes (PIB), of different molecular weights, wherein each resultant mixture is a pressure-sensitive. Other useful rubber based pressure-sensitive adhesives include hydrocarbon polymers such as natural and synthetic polyisoprene, polybutylene and polyisobutylene, styrene/butadiene polymers styrene-isoprene-styrene block copolymers, hydrocarbon polymers such as butyl rubber, halogen-containing polymers such as polyacrylic-nitrile, polytetrafluoroethylene, polyvinylchloride, polyvinylidene chloride, and polychlorodiene, and other copolymers thereof.

Other useful pressure-sensitive adhesives ("PSA") can include acrylic-based pressure-sensitive adhesives and silicone-based pressure-sensitive adhesives as described in U.S. Pat. Nos. 5,474,783, and 5,656,386. Suitable commercially available acrylic-based polymers can include adhesives are commercially available and include the polyacrylate adhesives sold under the trademarks Duro-Tak by National Starch and Chemical Corporation, Bridgewater, N.J., such as Duro-Tak 87-2194, Duro-Tak 87-2196, Duro-Tak 87-1197, 87-4194, 87-2510, 87-2097 and 87-2852. Other suitable acrylic-based adhesives are those sold under the trademarks Gelva-Multipolymer Solution (GMS) (Monsanto; St. Louis, Mo.), such as GMS 737, 788, 1151, 3087 and 7882.

Suitable silicone-based pressure-sensitive adhesives can include those described in Sobieski, et al., "Silicone Pressure Sensitive Adhesives," Handbook of Pressure-Sensitive Adhesive Technology, 2nd ed., pp. 508-517 (D. Satas, ed.), Van Nostrand Reinhold, New York (1989), incorporated by reference in its entirety. Other useful silicone-based pressure sensitive adhesives are described in the following U.S. Patents: U.S. Pat. Nos. 4,591,622; 4,584,355; 4,585,836; and 4,655,767. Suitable silicone-based pressure-sensitive adhesives are commercially available and include the silicone adhesives sold under the trademarks BIO-PSA 7-4503, BIO-PSA 7-4603, BIO-PSA 7-4301, 7-4202, 7-4102, 7-4106, and BIO-PSA 7-4303 by Dow Corning Corporation, Medical Products, Midland, Mich.

The amount of the polymer carrier can range from 2 to 99 wt %, preferably, 30 to 90 wt %, even more preferably 40 to 80 wt %.

The pressure-sensitive adhesives can be blended to modulate the solubility of the steroid in the carrier system such as described in the '783 patent. In a particularly preferred embodiment of the invention, the multiple polymer adhesive system comprises a pressure-sensitive adhesive blend of an acrylic-based polymer, a silicone-based polymer, and a soluble PVP (described below). The acrylic-based polymer and silicone-based polymer are preferably in a ratio by weight, respectively, from about 2:98 to about 96:4, more preferably from about 2:98 to about 90:10, and even more preferably about 2:98 to about 86:14. The amount of acrylic-based (also referred to broadly as a polyacrylate) polymer and silicone-based polymer (also referred to broadly as a polysiloxane) is adjusted so as to modify the saturation concentration of the steroid/corresponding steroid derivative in the ternary multiple polymer adhesive system in order to affect the rate of delivery of the steroid/corresponding steroid derivative from the system and through the skin. Other useful ranges include about 5-85% by weight of the acrylate-based polymer, 10-90% by weight of polyisobutylene and 5-95% by weight of silicone-based polymer.

The transdermal drug delivery system can also contain agents known to accelerate the delivery of the steroid/corresponding steroid derivative through the skin. These agents have been referred to as skin-penetration enhancers, accelerants, adjuvants, and sorption promoters, and are collectively referred to herein as "enhancers" and are described in U.S. Pat. No. 6,221,383. They can include polyhydric alcohols such as dipropylene glycol, propylene glycol, and polyethylene glycol which enhance steroid/steroid derivative solubility; oils such as olive oil, squalene, and lanolin; fatty ethers such as cetyl ether and oleyl ether; fatty acid esters such as isopropyl myristate which enhance steroid/corresponding steroid derivative diffusibility; urea and urea derivatives such as allantoin which affect the ability of keratin to retain moisture; polar solvents such as dimethyldecylphosphoxide, methyloctylsulfoxide, dimethyllaurylamide, dodecylpyrrolidone, isosorbitol, dimethylacetonide, dimethylsulfoxide, decylmethylsulfoxide, and dimethylformamide which affect keratin permeability; salicylic acid which softens the keratin; amino acids which are penetration assistants; benzyl nicotinate which is a hair follicle opener; and higher molecular weight aliphatic surfactants such as lauryl sulfate salts which change the surface state of the skin and drugs administered. Other agents include oleic and linoleic acids, ascorbic acid, panthenol, butylated hydroxytoluene, tocopherol, tocopheryl acetate, tocopheryl linoleate, propyl oleate, and isopropyl palmitate. Particularly preferred are combinations of polyhydric alcohols such as glycerine, dipropylene glycol, butylene glycol, propylene glycol and one or more of oleyl alcohol and oleic acid.

In some embodiments, the invention can also include a plasticizer or tackifying agent is incorporated into the formulation to improve the adhesive characteristics of the pressure-sensitive adhesive composition. Such plasticizers or tackifying agents include: (1) aliphatic hydrocarbons; (2) mixed aliphatic and aromatic hydrocarbons; (3) aromatic hydrocarbons; (4) substituted aromatic hydrocarbons; (5) hydrogenated esters; (6) polyterpenes; and (7) hydrogenated wood rosins.

The tackifying agent employed is preferably compatible with the blend of polymers. In preferred embodiments, the tackifying agent is silicone fluid (e.g., 360 Medical Fluid, available from Dow Corning Corporation, Midland, Mich.) or mineral oil. Silicone fluid is useful for blends comprising polysiloxane as a major component. In other embodiments, where a synthetic rubber, for example, is a major component, mineral oil is a preferred tackifying agent.

For steroid/corresponding steroid derivative molecules which are not readily soluble in the polymer system, a co-solvent for the steroid/corresponding steroid derivative and polymer can be added. Co-solvents, such as lecithin, retinal derivatives, tocopherol, dipropylene glycol, triacetin, propylene glycol, saturated and unsaturated fatty acids, mineral oil, silicone fluid, alcohols, butyl benzyl phthalate, and the like are useful in the practice of the instant invention depending on the solubility of the steroid/corresponding steroid derivative in the multiple polymer adhesive system.

In addition to the use of the steroid/steroid derivative combinations to inhibit crystallization, other crystallization inhibiting agents can be used. One known agent is polyvinylpyrrolidone (PVP), preferably soluble PVP as described in detail in U.S. Pat. No. 6,221,383. The term "polyvinylpyrrolidone," or "PVP" refers to a polymer, either a homopolymer or copolymer, containing N-vinylpyrrolidone as the monomeric unit. Typical PVP polymers are homopolymeric PVPs and the copolymer vinyl acetate vinylpyrrolidone. The homopolymeric PVPs are known to the pharmaceutical industry under a variety of designations including Povidone, Polyvidone, Polyvidonum, Polyvidonum solubile, and Poly(1-vinyl-2-pyrrolidone). The copolymer vinyl acetate vinylpyrrolidone is known to the pharmaceutical industry as Copolyvidon, Copolyvidone, and Copolyvidonum. The term "soluble" when used with reference to PVP means that the polymer is soluble in water and generally is not substantially cross-linked, and has a molecular weight of less than about 2,000,000. The PVP usable with the present invention, preferably has a molecular weight of about 2,000 to 1,100,000, more preferably 5,000 to 100,000, and most preferably 7,000 to 54,000.

The amount and type of PVP required in the foregoing preferred embodiment will depend on the quantity and type of steroid/corresponding steroid derivative present in the adhesive, as well as the type of adhesive, but can be readily determined through routine experimentation. Typically, the PVP is present in an amount from about 1% to about 20% by weight, preferably from about 3% to about 15% by weight. However, the amount of PVP can be higher than 20% for example, up to 40%, depending on the particular steroid/corresponding steroid derivative used and on the desired properties of the blend. One commercially useful PVP is sold under "Kollidon," such as "Kollidon 10," "Kollidon 17PF," "Kollidon 25," "Kollidon 90," "Kollidon 30," and "VA 64" a trademark of BASF AG, Ludwigshafen, Germany. Another useful PVP is sold under Kollidon CL-M also a trademark of BASF AG.

The compositions of this invention may further be provided with various thickeners, fillers and other additives known for use with transdermal drug delivery systems. Where the composition tends to absorb water, for example, when lecithin is used as a co-solvent, hydrophilic substances are especially useful. One type of hydrophilic substance which has been successfully employed is clay. The addition of clay has been found to improve adhesiveness in transdermal formulations without reducing the rate of steroid/steroid derivative delivery. Suitable clays include aluminum silicate clay, kaolinite, montmorillonite, atapulgite, illite, bentonite, halloysite and the like.

A device, or individual dosage unit, of the present invention can be produced in any manner known to those of skill in the art. After the dermal composition is formed, it may be brought into contact with the backing layer in any manner known to those of skill in the art. Such techniques include calender coating, hot melt coating, solution coating, etc. Of course, backing materials are well known in the art and can comprise plastic films of polyethylene, vinyl acetate resins, ethylene/vinyl acetate copolymers, polyvinyl chloride, polyurethane, and the like, metal foils, non-woven fabric, cloth and commercially available laminates. The backing material generally has a thickness in the range of 2 to 1000 micrometers and the dermal composition is generally disposed on backing material in a thickness ranging from about 12 to 250 micrometers thick.

Suitable release liners are also well known in the art and include the commercially available products of Dow Corning Corporation designated Bio-Release®. liner and Syl-off® 7610 liner. For preferred embodiments in which a polysiloxane is part of the multiple polymeric adhesive system, the release liner must be compatible with the silicone adhesive. An example of a suitable commercially available liner is 3M's 1022 Scotch Pak.® The configuration of the transdermal delivery system of the present invention can be in any shape or size as is necessary or desirable. Illustratively, a single dosage unit may have a surface area in the range of 1 to 200 $cm^2$. Preferred sizes are from 5 to 60 $cm^2$.

In a preferred method aspect of the invention where the carrier is a flexible, finite polymer, one or more polymers are blended, optionally with PVP to result in a pressure-sensitive adhesive composition, or transdermal drug delivery system adhesive system (with incorporated steroid:corresponding steroid derivative), which controls delivery of an incorporated steroid:corresponding steroid derivative and through the epidermis. In a preferred embodiment of the invention, a transdermal drug delivery system is prepared by mixing a soluble PVP, polyacrylate, polysiloxane, steroid/corresponding steroid derivative, optional enhancer(s), co-solvent(s), and tackifying agents, if needed, in an appropriate volatile solvent(s), then casting the mixture and removing the solvent(s) by evaporation to form a film. Suitable volatile solvents include, but are not limited to, alcohols such as isopropanol and ethanol; aromatics such as xylenes and toluene; aliphatics such as hexane, cyclohexane, and heptane; and alkanoic acid esters such as ethyl acetate and butyl acetate.

An exemplary general method for the preparation of an embodiment is as follows:

1. Appropriate amounts of solvent(s), optional enhancer(s), optional PVP and organic solvent(s) (for example toluene) are combined and thoroughly mixed together in a vessel.

2. The steroid:corresponding steroid derivative is then added to the mixture and agitation is carried out until the steroid/steroid derivative is uniformly mixed in.

3. Appropriate amounts of polymer are then added to the steroid/corresponding steroid derivative mixture, and thoroughly mixed.

4. The formulation is then transferred to a coating operation where it is coated onto a protective release liner at a controlled specified thickness. The coated product is then passed through an oven in order to drive off all volatile processing solvents.

5. The dried product on the release liner is then joined to the backing material and wound into rolls for storage.

6. Appropriate size and shape "systems" are die-cut from the roll material and then pouched.

The order of steps, the amount of the ingredients, and the amount and time of agitation or mixing may be importance process variables which will depend on the specific polymers, steroid/corresponding steroid derivative, cosolvents, and enhancers used in the formulation. These factors can be adjusted by those skilled in the art, while keeping in mind the object of providing a uniform product. It is believed that a number of other methods, including changing some of the order of steps, can be carried out and will give desirable results. In addition to having various shapes, the dosage units produces may come in various sizes. A surface area in the range of 1 to 200 square centimeters is contemplated, and the presently preferred sizes are: 5, 10, 15, 20, 30, 30 and 60 are centimeters.

EXAMPLES

The following specific examples are included as illustrative of transdermal delivery systems and compositions within the contemplation of the invention. These examples are in no way intended to be limiting of the scope of the invention. The weights percentages in the examples are based on dry weight of the system, unless other noted. In the figures, "NET" stands for norethindrone, and "NETA" stands for norethindrone acetate.

The following commercially available adhesives were used in the examples: "Duro-Tak 87-2287" is a trademark of NATIONAL STARCH AND CHEMICAL CORPORATION, Bridgewater, N.J. for polyacrylate adhesives in organic solutions.

"Bio-PSA 7-4603" is a trademark of DOW CORNING CORPORATION, MEDICAL PRODUCTS, Midland, Mich. for polysiloxane adhesives in organic solutions.

"Gelva-Multipolymer Solution (GMS) 737 and 788" are trademarks of the Monsanto Company, Saint Louis, Mo. for polyacrylate adhesives in organic solution.

"KOLLIDON 30 and VA 64" are trademarks of BASF Aktiengesellschaft, Ludwigschaften, Germany for polyvinylpyrrolidone polymers and the vinyl acetate/vinylpyrrolidone copolymer.

Example 1 and Comparative Example 1

A transdermal delivery composition was prepared with the following ingredients:

| | |
|---|---|
| Norethindrone | 1.2% |
| Estradiol | 0.9 |
| Norethindrone Acetate | 2.5 |
| PVP/ VA Copolymer (VA64) | 15.0 |
| Acrylic PSA (GMS737) | 5.0 |
| Oleic Acid | 3.0 |
| Dipropylene Glycol | 9.0 |
| Silicone PSA (7-4603) | 63.4 |

Flux of the steroids through the cadaver skin in vitro from the formulation of Example 1 is shown in FIG. 1 as triangles (Δ and ▲). Also shown as a comparative example ("CE") is the flux for the commercially available CombiPatch™ product that contains only estradiol and norethindrone acetate, which are shown as circles (○ or ●). As FIG. 1 indicates, the flux for the combined norethindrone/norethindrone acetate of Example 1 was significantly higher than norethindrone acetate alone of the CombiPatch™ product, while the flux of estradiol was unaffected. The flux of estradiol was approximately the same.

Example 2 and Comparative Examples (CE) 2

Transdermal steroid/corresponding steroid derivative delivery compositions were prepared with the following ingredients:

| Formulation | CE 2-1 | CE 2-2 | Ex. 2 |
|---|---|---|---|
| Norethindrone | 1.2% | 0% | 1.2% |
| Estradiol | 0.9 | 0.9 | 0.9 |
| Norethindrone Acetate | 0 | 2.5 | 2.5 |
| PVP/ VA Copolymer (VA64) | 15.0 | 15.0 | 15.0 |
| Acrylic PSA (GMS788) | 5.0 | 5.0 | 5.0 |
| Oleic Acid | 3.0 | 3.0 | 3.0 |
| Dipropylene Glycol | 9.0 | 9.0 | 9.0 |
| Silicone PSA (7-4603) | 65.9 | 64.6 | 63.4 |

Figure 2:
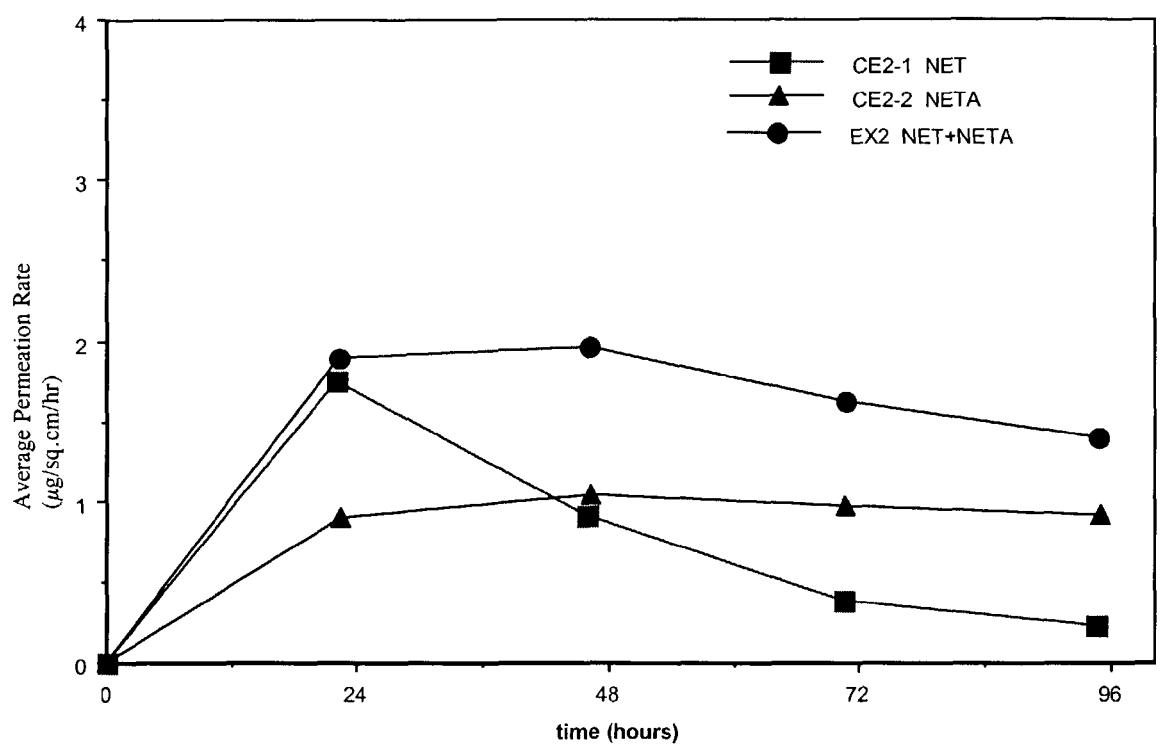
FIG. 2 is a graph illustrating the flux of norethindrone acetate from a composition containing norethindrone acetate and estradiol, combined norethindrone/norethindrone acetate from a composition containing norethindrone/norethindrone acetate and estradiol, and norethindrone from a composition containing norethindrone and estradiol.

Flux of the combined norethindrone/norethindrone acetate through the cadaver skin in vitro from the formulation of Example 2 is shown in FIG. 2 as circles (●). Also shown are comparative examples that contained only norethindrone and norethindrone acetate, which are shown as squares (■) and triangles (▲), respectively. As FIG. 2 indicates, the flux for the combined norethindrone/norethindrone acetate was significantly higher than either norethindrone or norethindrone acetate alone, in essentially in the same carrier compostion.

Example 3 and Comparative Examples 3

A transdermal steroid/corresponding steroid derivative delivery composition was prepared with the following ingredients:

| | |
|---|---|
| testosterone | 6.0% |
| testosterone acetate | 3.0 |
| PVP Kollidon 30 | 12.0 |
| acrylic PSA (GMS788) | 5.0 |
| oleic Acid | 3.0 |
| dipropylene Glycol | 9.0 |
| silicone PSA (7-4603) | 63.4 |

Figure 3:
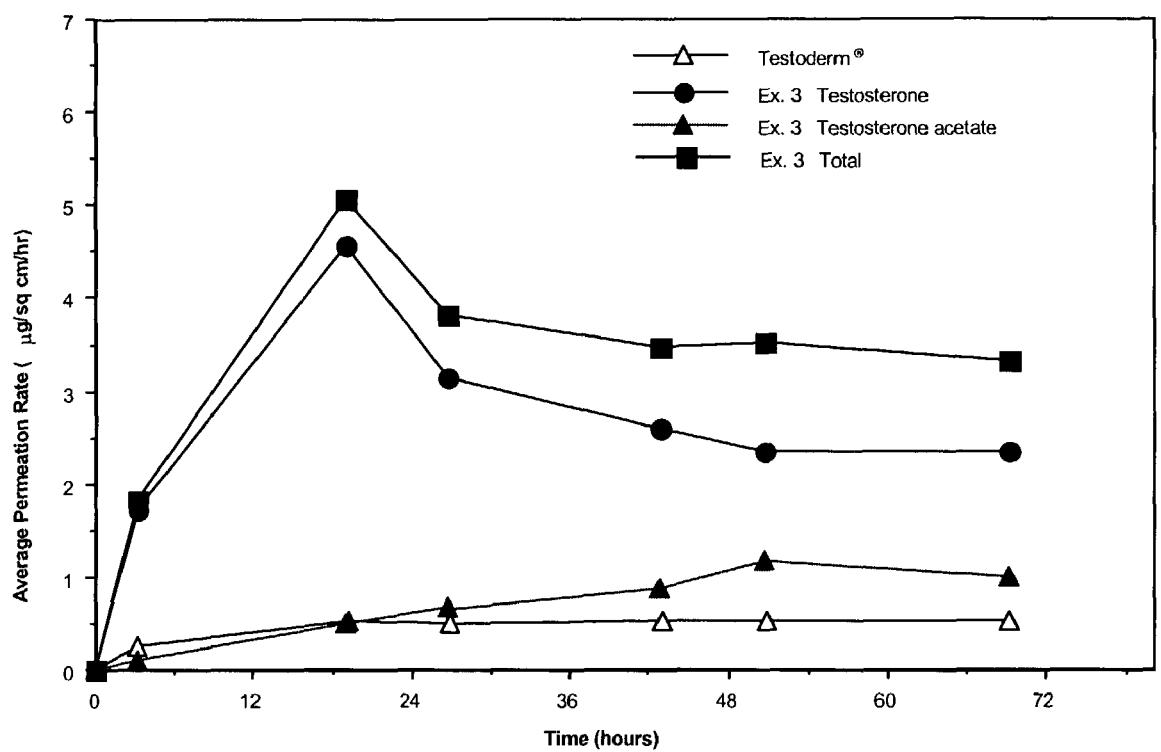
FIG. 3 is a graph illustrating the drug flux of combined testosterone/testosterone acetate from a composition containing testosterone/testosterone acetate, the flux of testosterone acetate from the same composition, the flux of testosterone from the same composition and the flux of testosterone from a transdermal drug delivery system called Testoderm® sold by Alza, Inc.

Flux of the combined testosterone/testosterone acetate through the cadaver skin in vitro from the formulation of Example 3 is shown in FIG. 3 as squares (■). Also shown are the separate flux of testosterone and testosterone acetate from the formulation of Example 3, shown as circles (●) and dark triangles (▲), respectively. Also shown is the flux of a commercially available testosterone composition sold under the trademark Testoderm® sold by Alza, Inc., shown as open triangles (Δ). As FIG. 3 indicates, the flux for the combined testosterone/testosterone acetate of Example 3 was significantly higher than the Testoderm® composition. Also, the individual fluxes of the testosterone and testosterone acetate of Example 3 were each greater than the flux of Testoderm® and accordingly demonstrate that each drug entity is being delivered in an amount sufficient to provide a physiological effect.

Example 4 and Comparative Examples 4

Transdermal steroid/steroid derivative delivery compositions were prepared with the following ingredients:

| | Ex 4-1 | Ex. 4-2 | Ex. 4-3 | Ex. 4-4 |
|---|---|---|---|---|
| Estradiol | 4% | 4% | 4% | 4% |
| Estradiol Acetate | — | 2.5 | — | — |
| Estradiol Enanthate | — | — | 2.5 | — |
| Estradiol Propionate | — | — | — | 2.5 |
| Kollidon 30 | 3 | 3 | 3 | 3 |
| Oleyl Alcohol | 6 | 6 | 6 | 6 |
| Dipropylene Glycol | 9 | 9 | 9 | 9 |
| Duro-Tak 87-2287 | 7 | 7 | 7 | 7 |
| Silicone PSA 7-4603 | 71 | 68.5 | 68.5 | 68.5 |

Examples 4-1 and 4-2 had crystals after 3 days. Examples 4-3 and 4-4 had no crystals at 13 days. From these results the acetate ester of estradiol is not as effective in inhibiting crystals, whereas, the propionate and enanthanate are effective in inhibiting crystals.

While a number of preferred embodiments of the present invention have been described, it should be understood that various changes, adaptations and modifications may be made therein without departing from the spirit of the invention and the scope of the appended claims.

The invention claimed is:

1. A composition for the transdermal delivery of a drug resulting from an admixture comprising:
   a therapeutically effective amount of a drug that includes a steroid and a corresponding steroid derivative that provides a source of therapeutically active steroid; and
   a pharmaceutically acceptable carrier,
   wherein the steroid and the corresponding steroid derivative are present in a weight/weight ratio of from 10:1 to 1:10 steroid:corresponding steroid derivative,
   and wherein said steroid is selected from the group consisting of anabolic steroids, androgenic steroids, glucocorticoids and mineralcorticoids.

2. A composition according to claim 1, wherein the ratio is from 6:1 to 1:6.

3. A composition according to claim 1, wherein the corresponding steroid derivative is a steroid ester.

4. A composition according to claim 1, wherein the carrier is a flexible, finite composition that includes at least one polymer.

5. A composition according to claim 4, wherein the flexible, finite composition comprises at least one of an acrylic-based polymer and a silicone-based polymer.

6. A carrier composition according to any one of claim 4 or 5, wherein the flexible, finite composition comprises a pressure-sensitive adhesive.

7. A composition according to claim 1, wherein composition further comprises an enhancer.

8. A composition according to claim 7, wherein the enhancer comprises dipropylene glycol and one or more of oleyl alcohol or oleic acid.

9. A composition according to claim 4, wherein the steroid and the corresponding steroid derivative are present in an amount of up to 20 wt %, based on the total composition.

10. A composition according to claim 4, wherein the steroid and the corresponding steroid derivative are present in an amount of up to 10 wt %, based on the total composition.

11. A composition according to claim 1, wherein the ratio from is 1:1 to 3:1.

12. A composition according to claim 1, wherein the ratio is from 3:2 to 5:2.

13. A composition according to claim 1, wherein the ratio is about 2:1.

14. A composition according to claim 1, wherein the steroid comprises an androgenic steroid selected from the group consisting of boldenone, fluoxymesterone, mestanolone, mesterolone, methandrostenolone, 17-methyltestosterone, 17.alpha.-methyltestosterone 3-cyclopentyl enol ether, norethandrolone, normethandrone, oxandrolone, oxymesterone, oxymetholone, prasterone, stanlolone, stanozolol, testosterone, testosterone 17-chloral hemiacetal and tiomesterone.

15. A composition according to claim 3, wherein the composition further comprises an additional steroid.

16. A composition according to claim 15, wherein the additional steroid is an estrogen.

17. A composition according to claim 16, wherein the estrogen is selected from the group consisting of: conjugated estrogenic hormones, equilenin, equilin, estradiol, estradiol benzoate, estradiol 17β.-cypionate, estriol, estrone, ethinyl estradiol and mixtures thereof.

18. A method of making a dermal composition according to claim 1, comprising forming a mixture of the steroid, steroid derivative and carrier.

19. A composition for the transdermal delivery of a drug resulting from an admixture comprising:
   a therapeutically effective amount of a drug that includes a steroid and a corresponding steroid derivative that provides a source of therapeutically active steroid; and
   a pharmaceutically acceptable carrier,
   wherein the steroid and the corresponding steroid derivative are present in a weight/weight ratio of from 10:1 to 1:10 steroid:corresponding steroid derivative,
   and wherein said steroid is estradiol and said steroid derivative is selected from the group consisting of estradiol enanthate, estradiol propiante, estradiol hemisuccinate (eutocol), estradiol undecylate, and estradiol ethers with a group on the 3 position of the steroid ring.

20. A composition according to claim 19, wherein the ratio is from 6:1 to 1:6.

21. A composition according to claim 19, wherein the corresponding steroid derivative is estradiol 3-methyl ether.

22. A composition according to claim 19, wherein the carrier is a flexible, finite composition that includes at least one polymer.

23. A carrier composition according to claim 22, wherein the flexible, finite composition comprises a pressure-sensitive adhesive.

24. A composition according to claim 22, wherein the flexible, finite composition comprises at least one of an acrylic-based polymer and a silicone-based polymer.

25. A composition according to claim 19, wherein composition further comprises an enhancer.

26. A composition according to claim 25, wherein the enhancer comprises dipropylene glycol and one or more of oleyl alcohol or oleic acid.

27. A composition according to claim 22, wherein the steroid and the corresponding steroid derivative are present in an amount of up to 20 wt %, based on the total composition.

28. A composition according to claim 22, wherein the steroid and the corresponding steroid derivative are present in an amount of up to 10 wt %, based on the total composition.

29. A composition according to claim 19, wherein the ratio is from 1:1 to 3:1.

30. A composition according to claim 19, wherein the ratio is from 3:2 to 5:2.

31. A composition according to claim 19, wherein the ratio is about 2:1.

32. A composition according to claim 21, wherein the composition further comprises an additional steroid.

33. A method of making a dermal composition according to claim 19, comprising forming a mixture of the steroid, steroid derivative and carrier.

* * * * *